(12) United States Patent
Xu et al.

(10) Patent No.: US 9,710,880 B2
(45) Date of Patent: Jul. 18, 2017

(54) USER-GUIDED SHAPE MORPHING IN BONE SEGMENTATION FOR MEDICAL IMAGING

(71) Applicant: Siemens Product Lifecycle Management Software Inc., Plano, TX (US)

(72) Inventors: Daguang Xu, Plainsboro, NJ (US); Shaohua Kevin Zhou, Plainsboro, NJ (US)

(73) Assignee: SIEMENS PRODUCT LIFECYCLE MANAGEMENT SOFTWARE INC., Plano, TX (US)

( * ) Notice: Subject to any disclaimer, the term of this patent is extended or adjusted under 35 U.S.C. 154(b) by 120 days.

(21) Appl. No.: 14/610,775

(22) Filed: Jan. 30, 2015

(65) Prior Publication Data

US 2016/0005166 A1    Jan. 7, 2016

Related U.S. Application Data

(60) Provisional application No. 62/020,636, filed on Jul. 3, 2014.

(51) Int. Cl.
*G06T 7/00* (2017.01)
*G06T 3/00* (2006.01)
(Continued)

(52) U.S. Cl.
CPC .......... *G06T 3/0093* (2013.01); *A61B 5/7475* (2013.01); *G06T 7/12* (2017.01);
(Continued)

(58) Field of Classification Search
CPC ......... G06T 7/0012; G06T 2207/30004; G06T 2207/30008; G06T 7/10; G06T 7/149; A61B 5/7475
See application file for complete search history.

(56) References Cited

U.S. PATENT DOCUMENTS

| 8,831,302 B2* | 9/2014 | Mahfouz | G06T 7/0028 382/128 |
| 2007/0197902 A1* | 8/2007 | Schutyser | G06T 7/0012 600/416 |

(Continued)

OTHER PUBLICATIONS

Josephson, Klas, Anders Ericsson, and Johan Karlsson. "Segmentation of medical images using three-dimensional active shape models." Scandinavian Conference on Image Analysis. Springer Berlin Heidelberg, 2005.*

(Continued)

*Primary Examiner* — Utpal Shah (57) ABSTRACT

A semi-automatic approach is used for user-guided bone segmentation in medical imaging. The user indicates a plurality of landmarks on an image of the bone. A processor morphs the same landmarks on a model of the bone to the user input landmarks on the image, resulting in a transform. This transform is then applied to the model to roughly segment the bone. The user may edit the resulting fit, and the processor then refines the edited fit, such as fitting the bone model to the scan data and avoiding any overlap with other bones. This user-guided segmentation may avoid the need for many samples to train a classifier for a fully automated approach while also avoiding the tedious outlining in a manual approach.

19 Claims, 5 Drawing Sheets

(51) Int. Cl.
  *G06T 11/00* (2006.01)
  *A61B 5/00* (2006.01)
  *G06T 19/20* (2011.01)
  *G06T 7/12* (2017.01)
  *G06T 7/149* (2017.01)
  *G06T 7/162* (2017.01)

(52) U.S. Cl.
  CPC .............. *G06T 7/149* (2017.01); *G06T 7/162* (2017.01); *G06T 11/003* (2013.01); *G06T 19/20* (2013.01); *G06T 2200/04* (2013.01); *G06T 2207/10081* (2013.01); *G06T 2207/20101* (2013.01); *G06T 2207/30008* (2013.01); *G06T 2219/2021* (2013.01)

(56) References Cited

U.S. PATENT DOCUMENTS

| | | | |
|---|---|---|---|
| 2010/0135546 A1* | 6/2010 | Cziria | G06T 7/0028 382/128 |
| 2011/0214279 A1* | 9/2011 | Park | B23P 17/04 29/592 |
| 2011/0286630 A1 | 11/2011 | Harder et al. | |
| 2012/0172700 A1 | 7/2012 | Krishnan et al. | |
| 2013/0077841 A1* | 3/2013 | Wu | G06K 9/6207 382/131 |
| 2014/0086465 A1 | 3/2014 | Wu et al. | |
| 2014/0093153 A1 | 4/2014 | Sofka et al. | |
| 2014/0161334 A1* | 6/2014 | Wang | G06K 9/00362 382/131 |
| 2014/0233820 A1* | 8/2014 | Wu | A61B 6/505 382/131 |
| 2015/0043774 A1* | 2/2015 | Harder | G06T 7/0046 382/103 |
| 2015/0227679 A1* | 8/2015 | Kamer | G06F 19/12 703/11 |

OTHER PUBLICATIONS

Lamecker, Hans, et al. "A 3D statistical shape model of the pelvic bone for segmentation." Medical Imaging 2004. International Society for Optics and Photonics, 2004.*

A. P. Harrison, et al., "IntellEditS: Intelligent Learning-Based Editor of Segmentations," Medical Image Computing and Computer-Assisted Intervention—MICCAI 2013, vol. 8151, pp. 235-242, 2013. (8 pages).

N. El-Zehiry, et al., "A Splice-Guided Data Driven Interactive Editing," Imaging and Computer Vision, Siemens Corp., pp. 1098-1101, 2013. (4 pages).

PCT Search Report dated Oct. 13, 2015, for Application No. PCT/US2015/038412, 13 pages.

* cited by examiner

USER-GUIDED SHAPE MORPHING IN BONE SEGMENTATION FOR MEDICAL IMAGING

RELATED APPLICATIONS

The present patent document claims the benefit of the filing date under 35 U.S.C. §119(e) of Provisional U.S. Patent Application Ser. No. 62/020,636, filed Jul. 3, 2014, which is hereby incorporated by reference.

TECHNICAL FIELD

This disclosure relates in general to the field of medical imaging, and, more particularly, to bone segmentation in medical imaging.

BACKGROUND

The number of orthopedic surgeries has been growing rapidly because of the aging population as well as development of medical technologies. Joint replacements, which have extended beyond hips and knees, are being performed on younger candidates with an increasing percentage of follow-on surgical revisions.

Bone segmentation from medical imaging assists planning for these orthopedic surgeries. The segmentation of bone tissue from a three-dimensional medical image, such as computed tomography (CT) image or a magnetic resonance (MR) image, allows engineering analysis for the replacement and optimization in individualized orthopedic surgical procedures.

Despite the large volume of research, the development of efficient and cost-effective algorithms for bone segmentation is still an open field. Most previous approaches are learning-based and rely heavily on a large database of annotated training images. However, it is very expensive and time-consuming to obtain a large amount of annotated images produced by human experts. Manual segmentation is also not optimal. Depicting the boundary of a bone slice-by-slice through a CT or other volume may be very tedious.

SUMMARY

By way of introduction, the preferred embodiments described below include methods, systems, instructions, and computer readable media for user-guided bone segmentation in medical imaging. A semi-automatic approach is used. The user indicates a plurality of landmarks on an image of the bone. A processor morphs the same landmarks on a model of the bone to the user input landmarks on the image, resulting in a transform. This transform is then applied to the model to roughly segment the bone. The user may edit the resulting fit, and the processor then refines the edited fit, such as fitting the bone model to the scan data and avoiding any overlap with other bones. This user-guided segmentation may avoid the need for many samples to train a classifier for a fully automated approach while also avoiding the tedious outlining in a manual approach.

In a first aspect, a method is provided for user-guided bone segmentation for medical imaging. Medical scan data representing a volume of a patient is received. The volume includes a bone. One or more images of the volume are generated on a display from the medical scan data. User selection of a plurality of points on the one or more images is received from a user input. The plurality of points is for locations distributed in the volume in three dimensions. A processor estimates a pose of the bone in the volume from a fit of the plurality of points to corresponding points in a model of the bone. The processor transforms the model of the bone as a function of the fit, and segments the bone from the volume with the transformed model.

In a second aspect, a non-transitory computer readable storage medium has stored therein data representing instructions executable by a programmed processor for bone segmentation for three-dimensional medical imaging. The storage medium includes instructions for determining a pose of a bone model in a scan volume of a bone, receiving, from a user input, an edit of the pose in the scan volume, refining a segmentation of the bone in the scan volume with the edited pose, altering the segmentation of the bone as refined, the altering avoiding overlap with another segmentation of another bone, and generating an image of the first and second segments after the minimizing.

In a third aspect, a method is provided for user-guided bone segmentation in medical imaging. A processor morphs predetermined landmarks of a bone shape to user input landmarks of a bone on an image of a volume of a patient. The morphing provides a non-rigid spatial transform. The processor transforms the bone shape with the non-rigid spatial transform and segments the bone from the volume with the transformed bone shape. An image of the bone is generated using a segmentation resulting from the segmenting.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DESCRIPTION OF EXEMPLARY EMBODIMENTS

User-guided shape morphing and automatic optimization efficiently segment bone. Efficient bone segmentation may substitute the prior knowledge obtained from training data and machine learning with the least amount of user input, while preserving the high accuracy and fast speed provided by automatic segmentation.

In one semi-automatic approach, user-guided shape morphing and automatic optimization are combined. The segmentation is first initialized using estimated pose parameters computed from user-specified corresponding landmark sets. Then, rough or user editing is applied to correct larger errors. The segmentation is further refined globally by a processor using a graph-based algorithm. Re-segmentation of the joint regions to avoid overlap with other bones and/or interactive editing approaches may be applied for local refinement. User-guided shape morphing or automatic optimization may be used alone.

For user-guided morphing, the pose parameters are computed from user-specified corresponding landmark sets instead of learned from a large training dataset. For example, the user specifies the position of several predefined anatomical landmarks by clicking on multi-planar reconstruction (MPR) views of the image volume. These parameters are then used to align a statistical shape or other bone model to the three-dimensional image or bone represented in the volume.

For optimization, multi-step refinements are used to improve the segmentation accuracy. The different steps may include both automatic optimization and user-guided editing. For example, a rough editing is first used to correct big errors in the shape initialization, such as translation, rotation, or scale errors. Then, automated global refinement using a graph-based algorithm is applied. The joint region of multi-bones is automatically re-segmented to avoid boundary overlaps of adjacent organs/structures. Finally, local refinement is implemented using interactive editing approaches. Any combination of automatic or user-guided refinements may be used.

Figure 1:
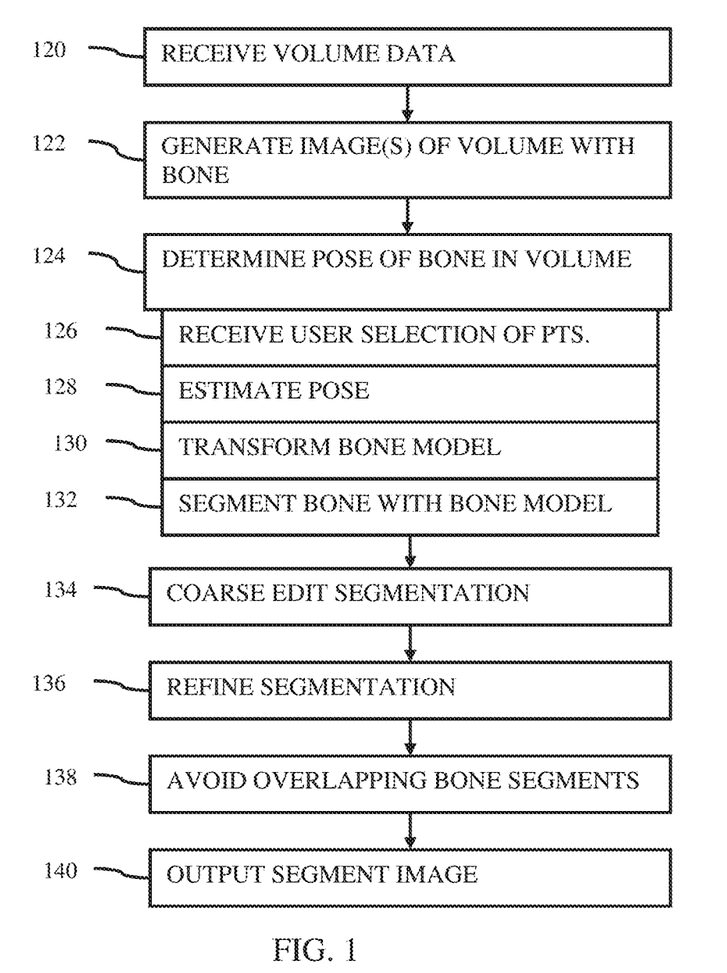
FIG. 1 is a flowchart diagram of another embodiment of a method for user-guided bone segmentation in medical imaging.

FIG. 1 shows one embodiment of a method for user-guided bone segmentation in medical imaging. The method is implemented using the system of FIG. 7, a medical imaging system, a workstation, a processor, a server, a computer, and/or a different system. In general, a processor receives three-dimensional data and performs the acts of the method to output an indication of locations for bones represented by the three-dimensional data.

An example of the method of FIG. 1 is represented in FIGS. 2-6. This example uses CT data representing a patient. The pelvis bone is included in the scan volume of the patient. The voxels or locations of the pelvis bone are segmented from the remaining tissue and/or bones represented in the volume. In other embodiments, other bones or organs may be segmented. In yet other embodiments, MR, ultrasound, PET, SPECT, fluoroscopic, x-ray, or other data representing the volume may be used instead of CT data.

The segmentation is performed on data representing a volume of the patient (e.g., voxels distributed in three dimensions). The segmentation is performed in three dimensions (e.g., x, y, and z in a Cartesian coordinate space). In alternative embodiments, the segmentation is performed in two dimensions.

Additional, different or fewer acts than shown in FIG. 1 may be provided. For example, acts for accessing other types of data, acts for transmitting an output, and/or acts for storing the segmentation are provided. As another example, acts 122-132 are performed without the further optimization of acts 134-138. In another example, act 124 is performed in any manner (e.g., with or without user-guided morphing and the corresponding acts 26-32) and any one or more of the optimization acts 134-138 are provided. Acts 120 and 140 may be optional.

The acts are performed in the order shown or different orders. The optimization acts 134-140 may be performed in any order, such as avoiding overlap before processor-based refinement of the segmentation or as part of the refinement.

In act 120, medical scan data, such as CT data, is received. CT scan data is used for describing the acts of FIG. 1, but other modalities may be used. The CT data is received by scanning a patient. An x-ray source and detector are rotated about a patient to acquire x-ray projections through a volume of the patient. The detected intensities are reconstructed into data representing the volume. In alternative embodiments, the CT data is received from memory, such as loading data from a DICOM archive system.

Figure 2:
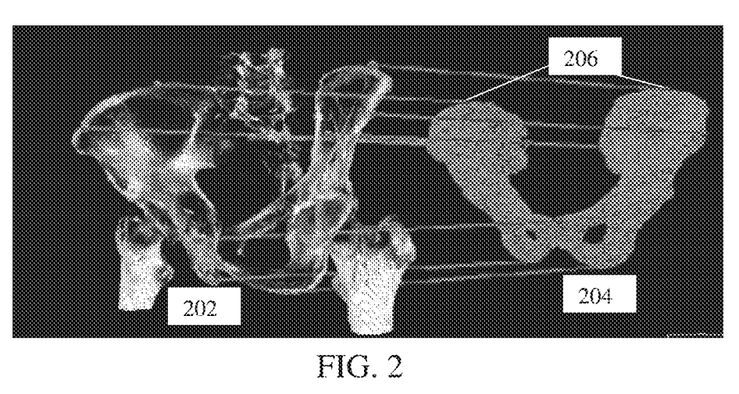
FIG. 2 shows an example of linking user entered landmarks on an image to the same landmarks on a bone model.

The CT data represents the patient. Parts or all of different organs, tissue types, bones, or other anatomical structure are represented by the data. For example, the data represents parts of the pelvis or the tibia and femur at the knee joint. Other tissue, such as other bones and/or soft tissue, may also be represented in the CT data. For example, FIG. 2 shows an example three-dimensional rendering of CT scan data that shows the pelvis bone but also includes the tops of the femurs and some vertebrae.

The 3D CT data has any format. In one embodiment, the 3D CT data is formatted in a regular grid in a Cartesian coordinate system. Different grid locations or voxels represent different spatial locations within the scanned volume of the patient. The voxels are distributed over three dimensions, such as having at least two voxels along each dimension. The 3D CT data as received or after reception may be processed to remove background, soft tissue, or tissue not of interest, and/or to perform other pre-segmentation operation. The example of FIG. 2 shows the bones with soft tissue removed or reduced in influence. The example of FIG. 3 includes the soft tissue in the imaging of the volume.

Figure 3:
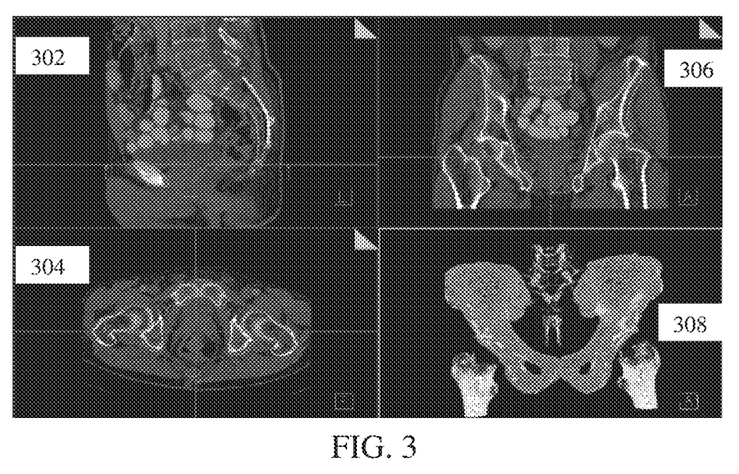
FIG. 3 shows an example of the bone model of FIG. 2 transformed to a multi-planar reconstruction.

In act 122, one or more images are generated of the volume. The medical scan data is used to generate any number of images on a display. In one embodiment shown in the example of FIG. 2, a three-dimensional rendering 202 of the volume is generated. The rendering 202 is a surface or projection rendering with or without shading and from any view direction. The user may set or alter the view direction or other rendering parameters. In another embodiment shown in the example of FIG. 3, MPR images 302, 304, and 306 are generated. Two-dimensional images 302, 304, and 306 of different planes through the volume are created, such as for three orthogonal planes. The user may translate and/or orient (e.g., rotate) the MPR planes relative to the volume and/or each other. Additional planes may be added for generating additional images. A three-dimensional rendering 308, as shown in FIG. 3, may be included with the MPR.

Other images may be generated as well. For example, a bone shape is provided. The bone shape is a model of the bone of interest. The model is created by an expert, is an average of multiple expert segmentations from other patients (e.g., mean shape), or is from a single segmentation from another patient. In one embodiment, the model is a statistical shape model including both a mean shape as well as statistics on deviations by location of the shape. The model is a mesh or other representation of the bone. The model may be the outline of the bone (e.g., hollow) or may be a solid defined by a mesh boundary.

An image of the model may be generated. FIG. 2 shows the image 204 of the model of the pelvis generated adjacent to the three-dimensional rendering 202 of the patient volume. The model is rendered using the same or different image generation as the volume, such as being a surface rendering from a same view direction.

In one embodiment, the image or images of the model are generated and displayed simultaneously with the image or images of the volume. FIG. 2 shows a side-by-side presentation. Alternatively, an image of the model is not provided or is displayed in sequence with the image of the volume of the patient.

In act 124, a pose of a bone model in the scan volume including the bone is determined. A processor, based on user guidance from a user input device, determines the pose of the bone model relative to the volume representing the patient. The pose is position, orientation, and/or scale. Any parameter structure for pose may be used. The pose includes the boundary of the bone. The pose may not include the boundary or otherwise segment particular locations, but instead indicates a parameterized or generalized location of the bone, such as with a bounding box, skeleton, or other parameterization.

The pose is determined in act 124 using the acts 126 and 128. The estimated pose is then used to initially segment in acts 130 and 132. The pose is determined in a parameter space of landmarks or points in the volume. The segmentation then further provides for pose estimation by transforming the other parts (i.e., non-landmark) of the bone model in act 130 for segmentation in act 132. Additional, different, or fewer acts may be used to determine the pose and segment. For example, acts 130 and 132 use the estimated pose of act 128 to segment, so may not be provided.

To determine the pose in act 124, the processor determines a spatial transform between landmarks input by a user in act 126. Shape initialization uses estimated pose parameters computed from two corresponding landmarks sets—one predetermined set for the bone model and another set of the same landmarks entered by the user in act 126. The predefined landmark set is called the "source" set.

Any landmarks may be used, such as points on the bone model at the bone tissue boundary, at changes in curvature, regularly spaced along the boundary, and/or at other anatomical locations of interest. One or more points may be for anatomy not part of the bone, such as anatomy of another bone or soft tissue that reflects the orientation, location, or scale of the bone. The landmarks may have clinical importance and/or may help to constraint the shape initialization. FIG. 2 shows a plurality of landmarks 206. The landmarks 206 are distributed in three dimensions along the outer edge or boundary of the pelvis model.

The landmarks may be highlighted for the user in the image of the bone model. Alternatively or additionally, the landmarks are described to the user. Any number of landmarks may be used, such as three or more landmarks not in a same plane.

The "source" landmarks are predefined or preselected by an expert on the bone model. The landmarks may be created or modified by the user and/or be different for different applications. For example, a user may believe that a specific landmark is more distinguishable, so adds the landmark to the bone model or changes an existing landmark. Different sets of possible source landmarks may be shown to the user for selection of a set. The user may add, remove, or alter the landmarks.

In act 126, the processor receives from a user input device user selection of landmark locations on the image or images of the volume. To simplify user input, the selection is of points rather than lines or curves. Tracing may be avoided. In alternative embodiments, one or more of the landmarks are defined as a line, curve, area, or volume. The user inputs and sizes a shape or other indicator of the non-point landmark. Tracing may be used.

The user inputs a plurality of landmark points. The landmarks are distributed in the volume in three-dimensions. The user sets the images to include locations of one or more landmarks. For example, the user changes a viewing direction of a rendering. As another example, the user alters plane positions in MPR imaging.

Once the image or images of the volume show one or more landmark locations, the user selects the location as being of a specific landmark. The user positions a cursor over the pixel showing the landmark location and clicks or activates selection of that location. For selection on a three-dimensional rendering, the processor may extrapolate the depth by finding where a bone surface represented in the volume intersects a projection along the viewing axis from the selected point. For MPR, the depth is defined by the location of the plane. Other user interface options may be used for selecting the landmarks by the user. A text or other file may include previous selection of one or more of the landmarks, so be used to select.

The user cycles through the source landmarks, indicating the corresponding locations on the image or images of the volume. For example, the user inputs and the processor receives the corresponding position of each "source" landmark point on the patient image by clicking on the MPR views of the volume. The corresponding points of all the points in the "source" landmark set make up the "destination" landmark set.

A one-to-one mapping is created between the points in the "source" and "destination" landmark sets, sequentially. The corresponding landmarks from the two sets are linked. A landmark in one set is linked to the same landmark in the other set. For example, FIG. 2 shows points highlighted on the rendering 204 of the model linked with points selected on the rendering 202 of the volume of the patient. Connecting lines graphically represent the linking. Other representations of the linking, such as labeling or color coding, may be used. Alternatively, no graphical representation of the linking is shown to the user.

To estimate the pose in act 128 of the bone in the volume, the processor fits the landmarks of the model to the landmarks of the bone represented in the volume. The corresponding or linked landmarks are used for fitting. The processor morphs the predetermined landmarks of the bone shape or model to the user input landmarks of the bone represented in the image 202 of the volume of the patient. Since the landmarks are distributed in more than one plane or in three dimensions, the fitting may be in three dimensions.

Any fitting may be used to estimate the pose. The fit provides a spatial transform. For example, the fit is deformable or a non-rigid spatial transform. A three-dimensional non-rigid transform is calculated to represent the fit or deformation of the source landmarks to match the destination landmarks. In alternative embodiments, a rigid transform is used.

The transform is calculated from the linked or connected points or landmarks. The differences between the landmarks of the model of the bone and the same landmarks input from the user for the bone represented in the volume are minimized with or without any constraints. In one embodiment, the pose parameters and shape space (PCA) parameters are estimated from the "source" and "destination" landmark sets by solving an optimization problem that minimizes the difference between the positions of the "destination" landmarks and the projected "source" landmarks using current transformation parameters in an iterative approach. One example cost function for minimization is:

$$\min_{t,r,s,\{\lambda_j\}} f(\{p_i, d_i\}; t, r, s, \{\lambda_j\}) = \qquad (1)$$

$$\min_{t,r,s,\{\lambda_j\}} \sum_i \left| t + T(s, r) \sum_j (p_i + u_{i,j}\lambda_j) - d_i \right| + \omega \sum_j \frac{\lambda_j^2}{\eta_j}$$

where: $\{p_i\}$ is the source landmark set, $\{d_i\}$ is the destination landmark set, t is the translation vector, T(s,r) is the similarity transform specified by a rotation r and scale s, $\{\lambda_j\}$ is the set of PCA shape coefficients, $\{u_{i,j}\}$ is the PCA shape basis corresponding to the source point $p_i$ and PCA coefficients $\lambda_j$, ω is a weight parameter, $\{\eta_j\}$ is the PCA shape coefficient from the statistical shape model, and |•| stands for the vector length: if x={$x_1, x_2, x_3$}, $|x|=\sqrt{x_1^2+x_2^2+x_3^2}$. Other cost functions may be used. Other transformation calculation methods may be used. For example, a thin-plate-spline is used to determine the spatial transform.

In act 130, the model of the bone is transformed using the fit. The processor applies the spatial transform from the estimated pose output from act 128 to spatially transform the model shape. The spatial transform representing the pose provides a non-rigid translation, rotation, and/or scale for the model to fit to the landmarks of the scan volume. The locations of the landmarks and other locations represented in the modeled bone shape are transformed with the non-rigid spatial transform. With the estimated pose parameters, the transformation is applied to all the points in the modeled shape to align the mesh or other parameterization of the model to the volumetric image. The various parts of the bone model, including the inner and outer regions of the bone, are transformed.

In act 132, the processor segments the bone from the volume using the transformed model. The transformed model shape is deformed based on the fitting of the landmarks to each other. As a result, the mesh or other parameterization of the model shape delineates locations of the bone from other locations. The transformed bone shape is used to segment the bone as represented in the scan volume.

The initial segmentation labels the voxels of the scan data. If a voxel belongs to the bone, the voxel is labeled as such. If the voxel does not belong to the bone, the voxel is labeled as such. The voxel labels indicate voxels within the bone and/or at the boundary of the bone. The locations of the bone in the volume are identified.

The segmentation is displayed to the user. FIG. 3 shows an example of an aligned or transformed mesh defining the locations of segmentation. The model is displayed as an overlay on an image or images (e.g., MPR) of the volume being segmented. In each of the MPR images 302, 304, and 306, an outline of the model or the boundary mesh intersecting the plane is shown over the image from the volume. The same approach is used for the volume rendering 308. Other representations of the segmentation may be provided to the user.

Since the parameters for model alignment are estimated from the landmark sets, the accuracy of the estimation as well as the alignment (e.g., transform) of the model depends highly on the accuracy of the position of the "destination" landmarks that are specified by the user. Using a small number (e.g., 3-10) of landmarks to make it easy on the user may result in less accuracy for the initial pose estimation and resulting segmentation. Due to variable accuracy in the manual selection of landmarks, further refinements are provided in acts 134-138. Furthermore, the pose estimation and initial segmentation is based on the landmarks, not all of the scan data. As a result, the initial segmentation is a generalization.

In act 134, the segmentation output in act 132 is edited. The processor receives user input from a user input device editing the segmentation. The pose is edited by the user using editing tools. The segmentation places the bone model relative to the volume for segmentation. This placement may be edited. This placement is edited by translation, rotation, and/or scaling. The user changes the placement based on the images 302-306. The edit is received by the processor as a rough or coarse edit of the pose in the scan volume.

Figure 4A:
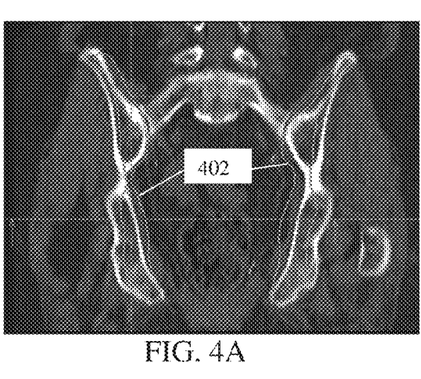
FIGS. 4A and B show an example of user input refinement of a pose determined by morphing.
Figure 4B:
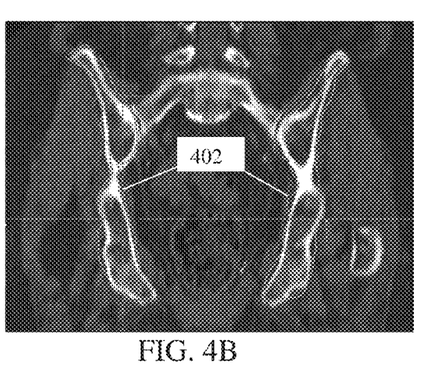

FIGS. 4A and B shows an example. The outlines 402 in FIG. 4A from the volume are offset along the x-axis. The user edits the segmentation by translating the outlines 402 along the x-axis as shown in FIG. 4B. The rough editing corrects for global or larger errors in the shape initialization result. This procedure is optional and is only used when a portion of the aligned mesh is far (e.g., gap noticeable to the user) from its correct position. Such gross errors may be difficult to be corrected by the remaining automated refinement procedures. Editing in a coarse level (e.g., editing just for translation, rotation, and/or scale) is usually sufficient, reducing the amount of user-input. Edits of the shape of the model or warping beyond translation, rotation, and/or scale may be provided.

Each independent or unconnected portion of the model represented may be separately edited. FIGS. 4A and B show two separate "FIG. 8" or "hour glass" shaped representations 402 of the model in the planar image. Both are shifted inward from the actual bone represented in the image. Both are translated in different directions for the editing. In alternative or additional embodiments, different or separate portions of the model represented in a given image may be linked for shifting together.

To translate, the user may drag the graphic representing the bone model. For example, the user clicks and drags the wire frame. To rotate, a rotation point may be assigned by the processor or input by the user once a rotation tool is activated. The user then clicks and rotates about the rotation point. To scale, a scale point may be assigned by the processor or input by the user once a scale tool is activated. By sliding (e.g., click and drag) the scale tool, the scale is altered while maintaining the aspect ratio. Alternatively, the aspect ratio may be altered as well. Other tools or editing approaches for the coarse adjustment may be used. In alternative embodiments, other editing tools than translation, rotation, or scaling are provided.

The editing is performed on a planar image (e.g., MPR) or a rendering of the volume. The change may be applied to the entire bone model. For example, translation is translation of the entire bone model. The change is reflected in all of the images currently displayed to the user. Alternatively, the change is localized. The bone model is warped or deformed with decreasing amounts of deformation with increasing distance. A change in one plane may result in a lesser or no change in other planes. The user may adjust the viewing direction and/or plane position to refine the coarse edit at different parts of the bone model.

In act 136, the segmentation after any coarse editing in act 134 is refined. The processor refines the segmentation automatically. With the initial or edited segmentation as an input, the refinement fits the bone model to the scan data of the volume. Further deformation from the edited pose is determined.

Any fitting may be used. The segmentation is altered, such as by filtering or other process. Any refinement may be used. The refinement may be optional.

In one embodiment, a graph-based energy function is applied by the processor. The bone model, as represented by mesh, is refined using a graph-based algorithm for segmentation. One example of such algorithm is the graph cuts segmentation with prior shape. The derived mesh of the edited segmentation is used as a prior shape, which is used to generate a confidence map that determines the possibility of a voxel maintaining its current label as bone or not bone. Any confidence map may be used, such as an output from a statistical shape model. The confidence map represents a likelihood, score, or level of confidence that a given voxel indicated as being part of the bone is part of the bone. In one embodiment, the confidence map is calculated based on distances of voxels from a bone boundary. For voxels labeled as being part of the bone, the distance to a nearest boundary location of the bone is calculated and used to determine the confidence. In general, the voxels within the object but further away from the boundary are more likely members of the object than voxels within the object but closer to the boundary. Distance maps are used as confidence maps with any function assigning confidence based on the distance, such as the inverse of distance alone being the confidence (or distance from the boundary being confidence where higher numbers represent greater confidence).

The segmenting is refined using the confidence map for the segmentation. A graph-based energy function is minimized based on the confidence map. One example approach refines the segmentation to better fit to the CT data. To better fit the CT data, the graph based energy function is represented as:

$$E(L) = \Sigma_N D_p(L_p) + \Sigma V_{p,q}(L_p, L_q) \quad (2)$$

where the sum of $D_p(L_p)$ is of the members of the volume P, the sum of $\Sigma V_{p,q}(L_p, L_q)$ is of the members p, q of the set of pairs of neighboring voxels N, where $L = \{L_p | p \in P\}$ is the binary labeling ($L_p \in \{0, 1\}$) of volume P, and $D_p(L_p)$ is the unary data term, which is defined as:

$$D_p(L_p) = L_p(1 - g(M(p))) + (1 - L_p)g(M(p)) \quad (3)$$

M(p) measures the signed shortest distance of voxel p to the boundary of the segmentation after boundary deformation. $M(p) > 0$ when p lies inside the segmentation (foreground), $M(p) < 0$ if p is outside the segmentation (background), and $M(p) = 0$ if p is located on the segmentation boundary. M can be viewed as the confidence map of the previous segmentation. The larger (or smaller) M(p) is, the more likely voxel p should be classified as the foreground (or background). When voxel p approaches the segmentation boundary, ($M(p) \approx 0$), label $L_p$ becomes more uncertain, and more likely to be updated by the segmentation refinement. $g(\cdot)$ is any function to map the distance to confidence, such as the sigmoid function defined as:

$$g(x) = 1/(1 + e^{-x/\tau}) \quad (4)$$

where $\tau$ is the parameter that controls the range of uncertainty of the previous segmentation result (e.g., 3-5 mm). In equation 2, N is the set of all pairs of neighboring voxels, and $V_{p,q}$ is the pair-wise interaction term:

$$V_{p,q} = \lambda e^{-((l_p - l_q)^2 / 2\sigma^2)} \delta(L_p \neq L_q) \quad (5)$$

where $\delta(\cdot)$ is the Kronecker delta function:

$$\delta(L_p \neq L_q) = 1 \text{ if } l_p \neq l_q \text{ and } 0 \text{ if } l_p = l_q,$$

and where $\lambda$ and $\sigma$ are the regularization parameter and contrast coefficient, respectively. Any values may be used such as 1-2 for $\lambda$ and 30-175 for $\sigma$. $l_p$ and $l_q$ denote the intensities of voxels p and q, respectfully. The pairwise term encourages the neighboring voxel with similar intensities to be assigned the same label.

The segmentation is refined by minimizing the energy function of equation 2. Any optimization of the energy function may be used, such as solving using the min-cut/max-flow algorithm with polynomial time complexity. Other solutions, functions, other graph-based cost functions, or other approaches to refinement may be used.

Figure 5A:
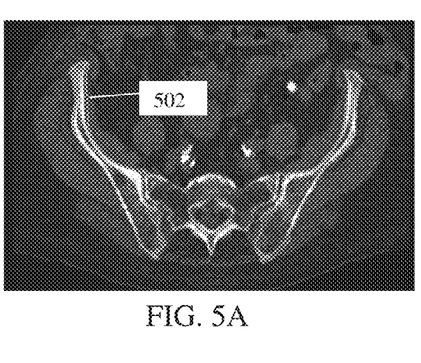
FIGS. 5A and B show an example of processor determined refinement of pose estimation.
Figure 5B:
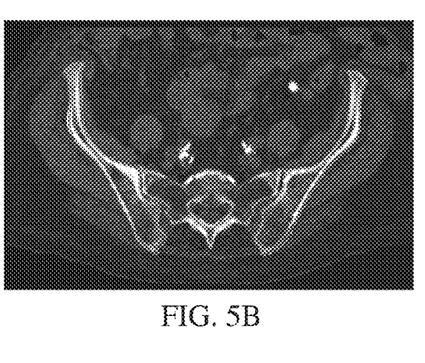

FIGS. 5A and B show an example of the improved result after graph-based segmentation refinement of act 136. A gap 502 between the bone of the volume represented in the image and the outline from the bone model is shown on FIG. 5A. Other gaps and/or regions where the outline or boundary of the bone model is within the bone may result from the initial segmentation. After the mesh of the bone model is refined using graph cuts, the gap is reduced or eliminated (see FIG. 5B). The result is a segment representing the bone as labeled in the CT data. Other segmentation may be used.

In act 138, another alteration of the segmentation of the bone is provided. After refinement by the processor (e.g., fitting the bone model to the scan data using a cost function), the segmentation is checked for overlap with other segmented bones. A joint joins multiple bones. The segmentation results for multiple bones may assign multiple labels to one voxel, if the segmentation of each bone is performed individually. The overlap error often occurs in the region of a joint where the bones are close to each other and the image contrast is not sufficient for a clear separation. Since a given voxel is to be assigned to only one bone, any voxels labeled as belonging to two bones is corrected to be for just one. In alternative embodiments, the segmentation is of a single bone, and overlap does not result. In this situation, this example further refinement is not provided.

To re-segment or alter a segmentation to avoid overlap with another segmentation, the processor applies a spatial constraint to enforce a spatial relationship in the region of the joint. Any overlap is identified and corrected. Re-segmentation is performed jointly to remove the overlap error. Joint re-segmentation incorporates a spatial constraint to prevent overlap. The segmentations are further refined using the spatial constraint, or the refinement of act 136 incorporates the spatial constraint.

A local overlap region is extracted. Only the scan data for the overlap is used or only the data in a region around the overlap is used. To make the re-segmentation more computationally efficient, the re-segmentation is only performed for voxels labeled as belonging to multiple objects or only for the overlap locations. The labels for the voxels identify the overlap. The labels of voxels are checked to determine whether a given voxel is labeled by the individual segmentations as belonging to more than one object. Alternatively, the re-segmentation is performed for a local region of a pre-determined or user set size around and including the overlapping locations. In yet other embodiments, the re-segmentation is performed for all locations or voxels.

By data masking other data or by removing the values for voxels in the region or overlap, the scan data for re-segmentation is extracted. Alternatively, the scan data is used without extraction so that adjacent voxels are available for re-segmentation calculations.

The results of the individual segmenting are adjusted jointly. The labels for the locations are altered to be exclusive to only one bone instead of two or more. Any criteria may be used to select one of multiple bones for a given voxel. The criteria are joint, so incorporates both bones into the consideration.

In one embodiment, confidence maps are used for joint re-segmentation. The confidence maps from the two or more bones indicate a likelihood of the location or voxel being a member of the respective bone. The bone with the highest confidence is selected as the object for the voxel. Other approaches to avoid non-smooth boundaries may be used for altering jointly.

Rather than mere selection, a graph-based energy function may be used. Pairwise co-segmentation with spatial constraints is used. A graph-based energy function constrained to label each voxel without overlap of the objects is minimized. The distances or the confidence are used in combination with the spatial constraint to alter the voxel labels to be exclusive to a single or no bone. With a specific spatial exclusion constraint introduced, the re-segmentation guarantees the complete removal of the overlap error.

The pair of objects are labeled as A and B. $L_A$ and $L_B$ stand for the labeling of bone A and B, respectively. Voxel p is inside bone A if $L_{A(p)}=1$ and otherwise if $L_{A(p)}=0$, likewise for bone B. The energy function of equation 2 is extended to the case of two objects as follows:

$$E(L_A, L_B) = E(L_A) + E(L_B) = \Sigma D_{A(p)}(L_{A(p)}) + \Sigma V_{A(p,q)}(L_{A(p)}, L_{A(q)}) + \Sigma D_{B(p)}(L_{B(p)}) + \Sigma V_{B(p,q)}(L_{B(p)}, L_{B(q)}) \quad (6)$$

where the sums of D are of the voxels in the volume P, the sums of V are of the voxels in the set N, and where all the symbols have the same meaning as in equation 2. Equation 6 is applied separately and in addition to the use of equation 2 in segmentation. Equation 6 is used for the joint re-segmentation, so M is now based on the segmentation results after refinement. As shown in equation 6, the minimization of $E(L_A, L_B)$ may be decomposed to the minimization of $E(L_A)$ and $E(L_B)$ separately because no interaction terms between $L_A$ and $L_B$ exist in the energy function of equation 6. Bones A and B are essentially segmented separately.

For joint re-segmentation, a spatial exclusion constraint exists between $L_A$ and $L_B$ because object A and B cannot overlap in the space. If $L_{A(p)}=1$, $L_{B(p)}$ must=0, and vice versa. This spatial constraint is incorporated into the energy function of equation 6 by adding the pairwise terms as follows:

$$E(L_A, L_B) = E(L_A, L_B) + \Sigma W(L_{A(p)}, L_{B(p)}) \quad (7)$$

where $W(L_{A(p)}, L_{B(p)}) = +\infty$ if $L_{A(p)} = L_{B(p)} = 1$ and otherwise is 0.

The optimal solution that minimizes the energy function $E^-(L_A, L_B)$ guarantees that $L_{A(p)}$ and $L_{B(p)}$ cannot be both 1 at the same time ($\forall p \in P$). The introduced pairwise term $W_{A(p),B(p)}(L_{A(p)}, L_{B(p)})$ is super-modular because $W(0,1)+W(1,0)<W(0,0)+W(1,1)$, so cannot be directly optimized via the min-cut/max-flow algorithm. To address this problem, the binary meaning of label $L_B$ is flipped to $L^-_B=1-LB$ or otherwise altered to avoid this ambiguity. The energy function $E^-(L_A, L_B)$ becomes sub-modular everywhere and the min-cut/max-flow solution may be used to find the optimal labeling of $L_A$ and $L_B$ jointly. Alternatively, a different minimization solution may be used.

Since the minimization is performed only for a local region associated with the overlap, only voxels in the overlap are altered. The adjustment is performed only for the identified overlap voxels. This avoids altering the labels of voxels outside of the overlap region. The joint segmentation with spatial constraints is applied only to a local overlap region generated from the initial segmentation of each individual bone. If there is no overlap in the initial segmentation, the joint segmentation is skipped. This results in efficient computation as compared to running joint segmentation with spatial constraint priors from the beginning (i.e., as compared to joint segmentation without separate individual segmentation).

Figure 6A:
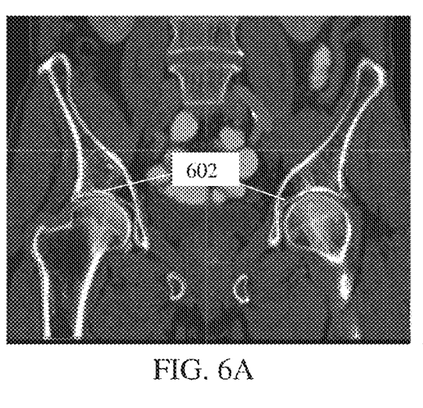
FIGS. 6A and B show an example of processor-based avoidance of overlap of bone segmentations.
Figure 6B:
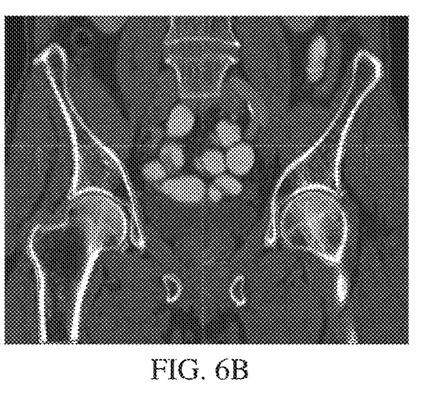

FIGS. 6A and B show an example of bone segmentation overlap and correction. The outlines of two meshes for two bones are shown overlapping at 602 on FIG. 6A. The bone models or meshes for the pelvis and the femur head overlap at both the left and right hip sockets. After re-segmentation to label each voxel as being for at most one bone, the segmentation is corrected as shown in FIG. 6B. The overlap of the outlines is removed.

Other refinements may be provided. Additional refinement procedures may also be applied to the resulting meshes to further improve the segmentation quality. For example, the graph cuts segmentation algorithm often produces holes in the meshes. Each hole is a small region of background surrounded by the foreground region (i.e., a non-bone region surrounded by bone). This is usually undesired since the bone structure may not have such feature. Where the hole is sized or in a location for which a hole is unexpected, a mesh hole filler is applied. The hole is identified and the voxels are relabeled as bone to correct this segmentation error. The mesh hole filler scans the mesh or segmentation mask to detect the locations of the holes and changes the labels of the voxels in the hole to foreground.

As another example further refinement, further manual or semi-automatic refinement may be provided. The segmentation quality may be further improved by refining the mesh or segmenting mask with interactive editing approaches. For example, the user traces part of the boundary. The processor then alters the mask to include the traced boundary. The processor may re-segment using the traced boundary as a prior for better fitting the bone model to the scan data. A splice-guided re-segmentation may be used. As another example, the user may select a region which should or should not be included in the segmentation. The bone model defining the segmentation may be altered by the processor to account for this user selection.

In act 140, an image is output. The image shows the segmented bone or bones. A graphic, highlighting, colorization, or other visual cue is added to or included in the image to distinguish the bone. For example, an image is rendered or a MPR is generated using the scan data representing the volume. The segmentation is used to colorize or otherwise distinguish the bone from other tissue and/or bones. Alternatively, an image just of the scan data from the bone segment is generated. The segmentation is used to mask out data not from the bone. The remaining data is used to generate the image.

Where multiple bones are segmented, the image may represent the multiple bone segments. After removing any overlap in the labeling, the different bones are shown together with or without added color or other highlighting to distinguish between the bones.

The image is a three-dimensional rendering to a two-dimensional image of the scan data from a user or processor selected viewing direction. The rendering may use surface, projection, or other rendering. In other embodiments, the image is a two-dimensional image representing a plane through the volume, such as provided with a MPR or user selected viewing plane.

Figure 7:
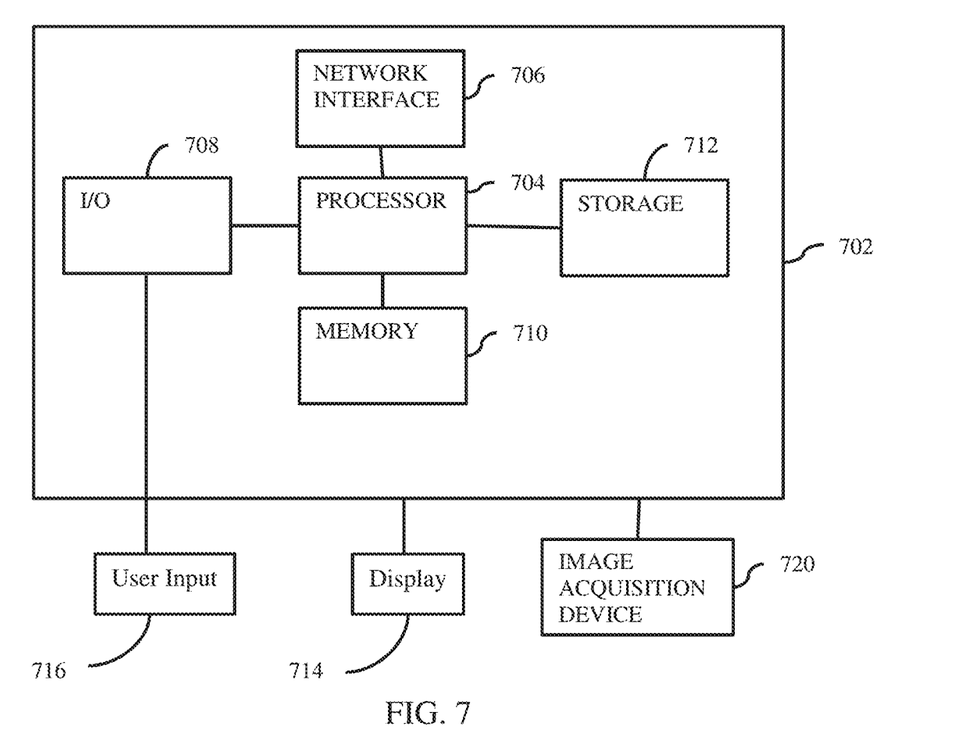
FIG. 7 is a block diagram showing one embodiment of a system for user-guided bone segmentation in medical imaging.

FIG. 7 illustrates an exemplary system or platform for automated user-guided bone segmentation in medical imaging. The system includes a computer 702, image acquisition device 720, user input device 716, and display 714. The computer 702 includes a processor 704, a memory 710, storage 712, input/output interface 708, and a network interface 706. The computer 702 with or without the display 714 and/or user input device 716 is a computer, laptop, tablet, workstation, server, CT workstation, or other processing device. The computer 702 is part of the image acquisition device 720 in one embodiment, but may be a separate device.

Additional, different, or fewer components may be provided. For example, multiple processors and/or other computer parts are provided. An implementation of an actual computer may contain other components. FIG. 7 is a high level representation of some of the components of such a computer 702 for illustrative purposes. As another example, the image acquisition device 720 is not provided.

The image acquisition device 720 is a CT scanner, an MR scanner, a PET system, a SPECT system, an ultrasound scanner, or other medical imaging modality. As a CT scanner, the image acquisition device 720 includes a source and detector. A gantry rotates the source and detector about a patient. A C-arm may be used instead of the gantry for CT-like imaging that produces CT data. The CT scanner scans the patient with x-rays. The processor 704 or other processor (e.g., of the CT scanner 720) reconstructs the CT data representing the volume from the detected x-ray projections. The reconstruction is to a three-dimensional Cartesian coordinate grid, but other coordinate systems may be used. The processor 704 or other processor uses the reconstructed scan data to generate images of the volume.

The image acquisition device 720 connects to the computer 702 to input image or scan data to the computer 702. The connection is a wireless or wired connection, such as over a communications network in a healthcare facility. The image acquisition device 720 and the computer 702 may instead be implemented as one device.

The user input device 716 is a keyboard, buttons, sliders, knobs, mouse, trackball, touchpad, touchscreen, combinations thereof, or any other now known or later developed user input device. The user enters information into the computer 702 with the user input device 716. For example, the user controls imaging, such as changing a viewing direction for three-dimensional rendering and/or plane positions for MPR. The user input device 716 is used to indicate landmark locations on an image or images generated from the scan data. The user input device 716 may be used for editing, such as course editing to translate, rotate, and/or scale a mesh or other bone shape for segmentation. Other inputs may be provided from the user input device 716, such as inputs for refining segmentation.

The user input device 716 connects with the input/output interface 708 of the computer 702. The connection is wired or wireless. The inputs received by the input device 716 are communicated to and received by the input/output interface 708 of the computer 702.

The display 714 is a CRT, LCD, flat panel, plasma, projector, printer, combinations thereof or any other now known or later developed display. Using a graphics processing unit or other hardware or software, the display 714 generates black and white or color pixels in a Cartesian or other coordinate format for presenting a graphical user interface, editing tools, medical image, segment information, a medical image with segment information, or combinations thereof. For example, the display 714 is configured by the processor 704 to generate the images of FIGS. 2-6, such as images rendered or reconstructed from scan data with overlaid outlines or graphics for the bone model or segmentation. The segment or segments identified by the processor and/or with the help of the user may be displayed. In alternative or additional embodiments, the segments are output to the memory 710, storage 712, a different memory, transmitted over a network, or provided to the processor 704 for further operations (e.g., surgical planning, implant design, or cutting guide design).

The processor 704 controls the overall operation of the computer 702 by executing computer program instructions which define such operation. The processor 704 is a general processor, applications specific integrated circuit, digital signal processor, field programmable gate array, multiple processors, analog circuit, digital circuit, network server, graphics processing unit, combinations thereof, or other now known or later developed device for performing segmentation. The processor 704 segments bone or other object based on user input of landmarks. The processor 704 uses user inputs to semi-automatically segment. The user inputs may be limited to landmarks, coarse pose edits, and/or other refinements of segmentation. The processor 704 uses the user inputs to segment initially, refine the segmentation as edited by the user, and/or to remove any overlapping segmentations. The processor 704 automatically performs some segmentation functions, such as estimating pose from user input landmarks and/or refining an initial segmentation using a fit to scan data.

The computer 702 also includes one or more network interfaces 706 for communicating with other devices via a network. Scan data may be acquired by transfer over the network rather than a direct connection with the image acquisition scanner 720.

The memory 710 and/or storage device 712 stores data, such as scan data, confidence maps, distances, models, source landmarks, input destination landmarks, images, or other information used for bone segmentation for three-dimensional imaging. Other data may be stored, such as data used for any stage of processing to segment.

The storage device 712 is an external or removable media, such as a flash drive or optical disk. The memory 710 is an internal memory, such as RAM, hard drive, or cache.

The computer 702, interacting with the acquisition imaging device 720, the user input 716, and the display 714, implements the acts of FIG. 1 or other acts. The computer program instructions may be stored in a storage device 712 (e.g., magnetic disk) and loaded into memory 710 when execution of the computer program instructions is desired. Thus, the acts of the methods described may be defined by the computer program instructions stored in the memory 710 and/or storage 712 and controlled by the processor 704 executing the computer program instructions. The memory 710 and/or storage 712 are a non-transitory computer readable storage medium storing data representing instructions executable by the programmed processor 704 for bone segmentation for three-dimensional medical imaging. The instructions for implementing the processes, methods, acts, and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

What is claimed is:

1. A method for user-guided bone segmentation in medical imaging, the method comprising:
receiving medical scan data representing a volume of a patient, the volume including a bone;
generating, on a display, one or more images of the volume from the medical scan data;
receiving, from a plurality of respective user inputs, a plurality of respective user selections of a plurality of respective points on the one or more images, the plurality of points being for locations distributed in the volume in three dimensions;
estimating, by a processor, a pose of the bone in the volume from a fit of the plurality of points to predetermined corresponding landmark points in a model of the bone;
transforming, by the processor, the model of the bone as a function of the fit; and
segmenting, by the processor, the bone from the volume with the transformed model.

2. The method of claim 1 wherein receiving the medical scan data comprises receiving the medical scan data representing the volume including the bone and other tissue.

3. The method of claim 1 wherein generating the one or more images comprises generating a multi-planar reconstruction, and wherein receiving the user selections comprises receiving selections of the points on the images of the multi-planar reconstruction.

4. The method of claim 1 wherein generating comprises generating a rendering of the volume and a rendering of the model, and wherein receiving the user selections comprises linking the corresponding points highlighted on the rendering of the model with the bone shown on the rendering of the volume.

5. The method of claim 1 wherein receiving the user selections comprises receiving where the plurality of points comprise landmarks of the bone, the predetermined corresponding landmark points being for the landmarks of the bone represented in the model.

6. The method of claim 1 wherein estimating comprises minimizing differences between the plurality of points and the predetermined corresponding landmark points.

7. The method of claim 1 wherein estimating comprises calculating a transform from the predetermined corresponding landmark points to the plurality of points, and wherein transforming comprises applying the transform to the model.

8. The method of claim 1 wherein transforming comprises non-rigidly translating, rotating, and/or scaling the model including locations other than the predetermined corresponding landmark points.

9. The method of claim 1 wherein segmenting comprises identifying locations for the bone in the volume, the locations being on or in the transformed model.

10. The method of claim 1 further comprising:
outputting an image showing the bone as segmented without other portions of the volume.

11. The method of claim 1 further comprising editing, from user inputs, the segmenting.

12. The method of claim 1 further comprising refining the segmenting using a graph-based energy function.

13. The method of claim 1 further comprising:
identifying an overlap of the segmenting of the bone with segmenting of another bone; and
correcting the overlap.

14. In a non-transitory computer readable storage medium having stored therein data representing instructions executable by a programmed processor for bone segmentation in three-dimensional medical imaging, the storage medium comprising instructions for:
receiving medical scan data representing a scan volume of a patient, the scan volume including a bone;
generating, on a display, one or more images of the scan volume from the medical scan data;
receiving, from a plurality of respective user inputs, a plurality of respective user selections of a plurality of respective user input points on the one or more images, the plurality of user input points being for locations distributed in the scan volume in three dimensions;
determining a pose of a bone model in a scan volume by morphing predetermined landmarks of the bone model to the user input points corresponding to the predetermined landmarks;
receiving, from at least one further user input, an edit of the pose in the scan volume;
refining a segmentation of the bone in the scan volume with the edited pose;
altering the segmentation of the bone as refined, the altering avoiding overlap with another segmentation of another bone; and
generating an image of the segmentation of the bone as refined.

15. The non-transitory computer readable storage medium of claim 14 wherein determining the pose comprises determining a spatial transform between the user input points and the predetermined landmarks of the bone model.

16. The non-transitory computer readable storage medium of claim 14 wherein receiving the edit comprises receiving translation, rotation, and/or scale edits of an outline of the bone model in the pose in a rendering with the scan volume.

17. The non-transitory computer readable storage medium of claim 14 wherein refining comprises applying a graph-based energy function.

18. A method for user-guided bone segmentation in medical imaging, the method comprising:
receiving medical scan data representing a volume of a patient, the volume including a bone;
generating, on a display, one or more images of the volume from the medical scan data;
receiving, from a plurality of respective user inputs, a plurality of respective user selections of a plurality of respective user input points on the one or more images, the plurality of user input points being for locations distributed in the volume in three dimensions;

morphing, by a processor, predetermined landmarks of a bone shape to the user input points corresponding to the predetermined landmarks, the morphing providing a non-rigid spatial transform;

transforming, by the processor, the bone shape with the non-rigid spatial transform;

segmenting, by the processor, the bone from the volume with the transformed bone shape; and generating an image of the bone using a segmentation resulting from the segmenting.

19. The method of claim 18 wherein morphing comprises morphing in three dimensions such that the non-rigid transform is a three-dimensional spatial transform.

\* \* \* \* \*